US005584286A

United States Patent [19]

Kippax

[11] Patent Number: 5,584,286

[45] Date of Patent: Dec. 17, 1996

[54] INTEGRATED BREATHING SYSTEM

[76] Inventor: John E. Kippax, 18 Mayhew Ave., Larchmont, N.Y. 10538

[21] Appl. No.: 292,048

[22] Filed: Aug. 18, 1994

Related U.S. Application Data

[63] Continuation of Ser. No. 3,609, Jan. 13, 1993, abandoned.

[51] Int. Cl.[6] .......................... A61M 15/00; A61M 16/00; A62B 7/00; A62B 18/02

[52] U.S. Cl. ................................ 128/200.24; 128/206.21; 128/207.14

[58] Field of Search ........... 128/201.15, 201.22–201.26, 128/204.18, 205.12, 205.18, 205.25, 205.26, 206.12, 206.15, 206.21, 206.27, 206.28, 207.11–207.13, 202.12, 207.14, 200.24

[56] References Cited

U.S. PATENT DOCUMENTS

| | | | |
|---|---|---|---|
| 428,592 | 5/1890 | Chapman . | |
| 718,785 | 1/1903 | McNary | 128/207.18 |
| 835,075 | 11/1906 | Mahaffy | 128/207.12 |
| 870,407 | 11/1907 | Anthony | 128/206.28 |
| 916,567 | 3/1909 | Leonard . | |
| 1,005,196 | 10/1911 | Gold et al. | 128/205.25 |
| 1,129,619 | 2/1915 | Zapf | 128/205.26 |
| 1,167,249 | 1/1916 | Arel | 128/205.26 |
| 1,239,634 | 9/1917 | Stuart | 128/203.26 |
| 1,331,297 | 2/1920 | Walker | 128/207.18 |
| 1,474,205 | 11/1923 | Mase . | |
| 1,632,449 | 6/1927 | McKesson | 128/206.24 |
| 1,931,989 | 10/1933 | Jennes . | |
| 2,460,604 | 2/1949 | Simcox . | |
| 2,810,386 | 10/1957 | Reed . | |
| 2,954,027 | 9/1960 | Marasco . | |
| 3,259,053 | 7/1966 | Steel . | |
| 3,278,114 | 10/1966 | Gibbs . | |
| 3,422,482 | 1/1969 | Hamrick . | |
| 3,657,740 | 4/1972 | Cialone . | |
| 4,055,173 | 10/1977 | Knab | 128/910 |
| 4,233,972 | 11/1980 | Hauff et al. . | |
| 4,394,861 | 7/1983 | Sciortino . | |
| 4,413,622 | 11/1983 | Austin . | |
| 4,440,164 | 4/1984 | Werjefelt | 128/205.25 |
| 4,649,912 | 3/1987 | Collins . | |
| 4,774,939 | 10/1988 | Disney . | |
| 4,840,169 | 6/1989 | Folsom | 128/910 |
| 4,906,261 | 3/1990 | Mohajer . | |
| 4,915,105 | 4/1990 | Lee . | |
| 5,014,693 | 5/1991 | Wright, II et al. | 128/204.18 |
| 5,018,519 | 5/1991 | Brown | 128/205.25 |

FOREIGN PATENT DOCUMENTS

| | | |
|---|---|---|
| 741127 | 2/1933 | France . |

*Primary Examiner*—Kimberly L. Asher
*Attorney, Agent, or Firm*—James Creighton Wray

[57] ABSTRACT

The integrated breathing system of the present invention incorporates a mask covering the nose and mouth, an intake having two side hoses and a central inlet tube, and a window mount. The two side hoses attach to the opposite sides of the mask and surround the user's head for stability, connecting in the rear to the central tube. The central tube extends oppositely to a connection with the window mount for communication with air on the other side of the window. The window mount can be a foam block, a clip or an adjustable block, and a fan or other air conditioning means can be incorporated for providing a positive air flow to the mask. The system is an inexpensive and simply constructed alternative to the expensive breathing systems used in work places.

27 Claims, 4 Drawing Sheets

FIG. 1
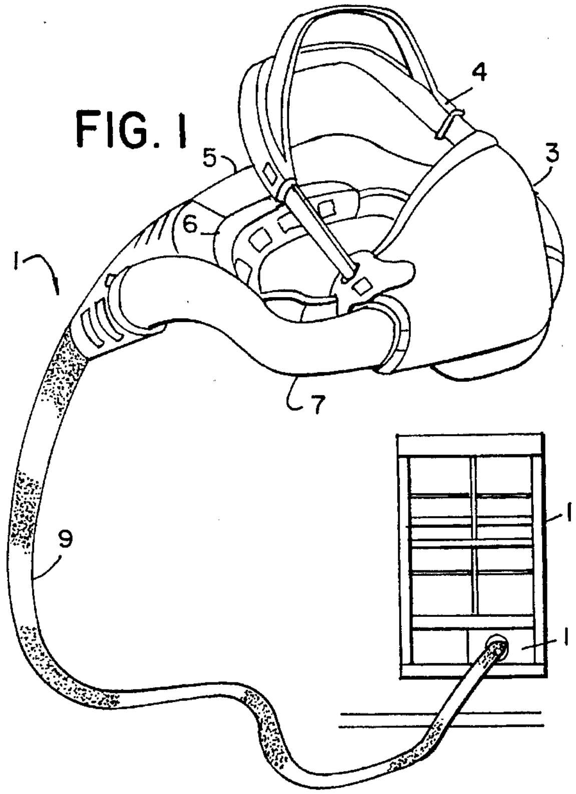
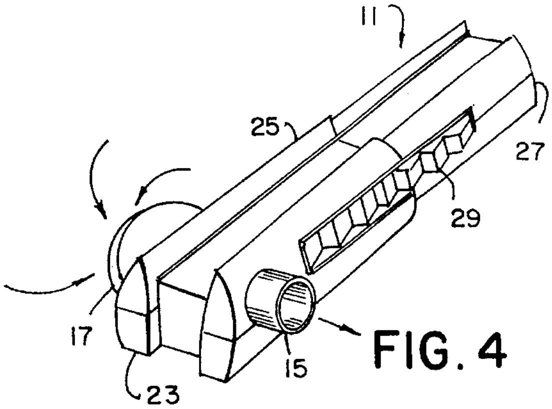
FIG. 4
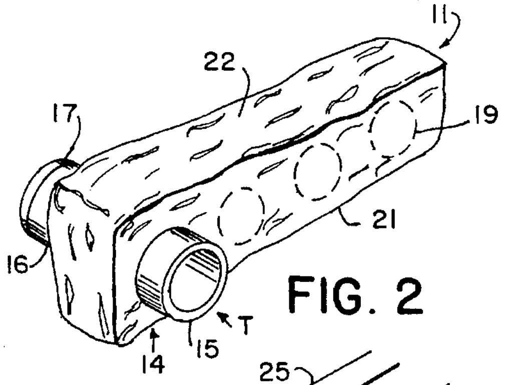
FIG. 2
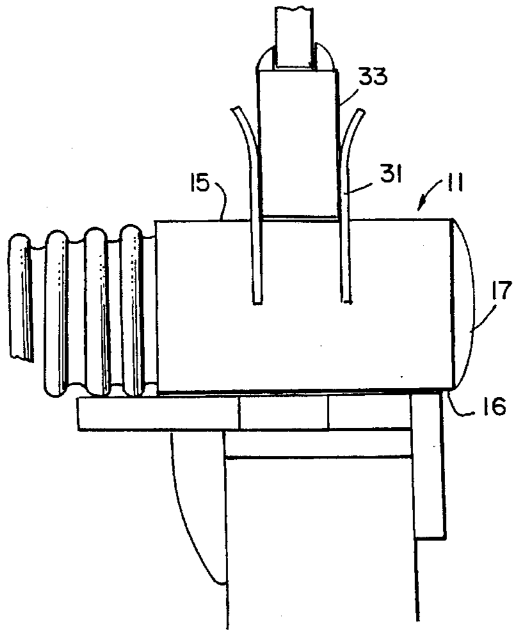
FIG. 5
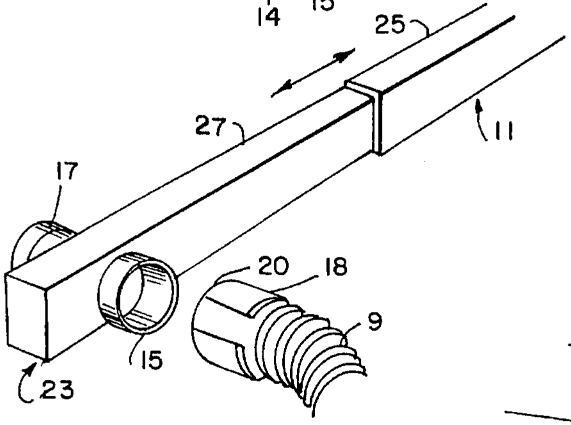
FIG. 3
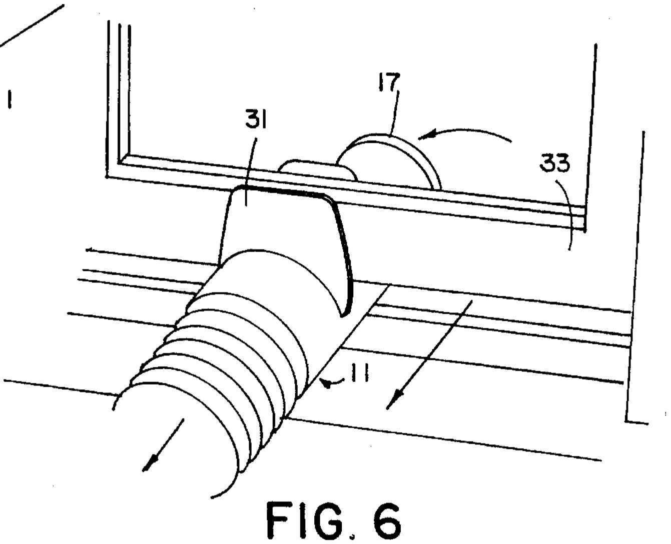
FIG. 6

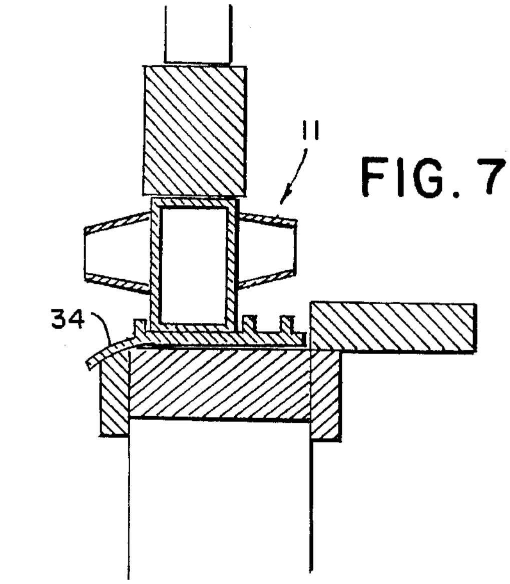
FIG. 7
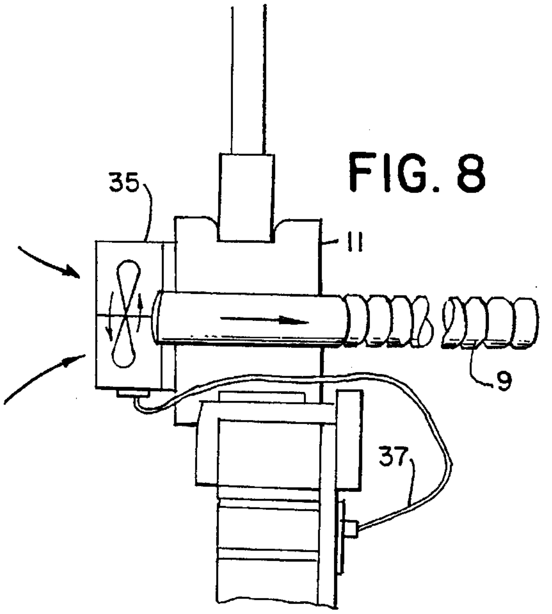
FIG. 8
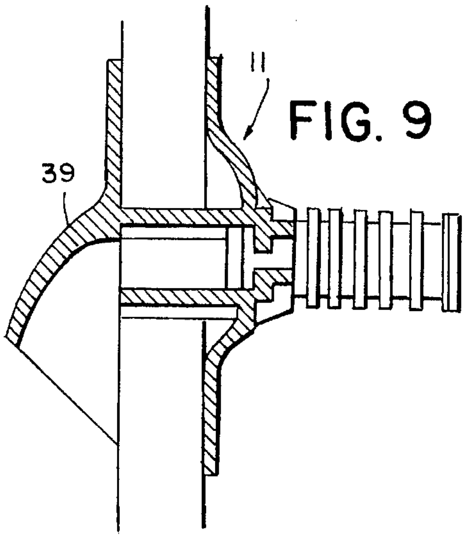
FIG. 9
FIG. 10
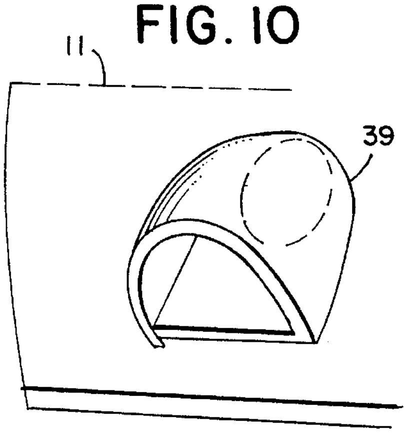
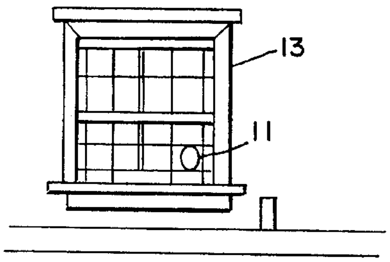
FIG. 11
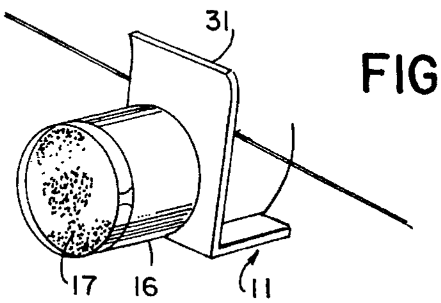
FIG. 12

INTEGRATED BREATHING SYSTEM

This Application is a Continuation of Ser. No. 08/003,609 filed Jan. 13, 1993, now abandoned.

BACKGROUND OF THE INVENTION

Suspended particulate by-products of work processes are a primary problem in many current work places. Stripping, spray-painting and sanding are examples of processes which throw minuscule particles of dust and other matter into the air, causing irritation and damage to unprotected workers' respiratory systems. Similarly, jobs such as demolition result in large quantities of often dangerous materials to be suspended within the work place. Vapors are also problems to the lungs and eyes in places such as auto body shops, where thinners and similar materials are used. Numerous other situations are known wherein individuals with respiratory ailments or immunodeficiencies require protection against inhaling contaminating substances. A primary example is a severe allergic reaction to dust.

Dust masks are readily available, inexpensive, easy to use and provide contour fit. However, dust masks have functional limitations. They often have poor fit and contamination levels are high. Dust masks only partially filter dust and certain particulates. Dust masks must be frequently replaced. They do not protect against vapors and gases.

Respirators with side mounted filters are commonly used. Adjustable straps hold a rubber face piece with rolled edges for comfort. Respirators are easy to find, and filters can be replaced for $5 to $25 per filter. The masks protect against most dust and limited ranges of vapors. They have durable construction. However, many dangerous toxins are not filtered, such as isocyanate containing finishes, i.e. all polyurethane paints and acrylics. Respirators with side mounted filters are hard on lungs. As the filters' useful life are extended, breathing becomes more difficult. It is difficult to determine when filters have lost effectiveness. Replacement of filters is expensive. Filters wear out rapidly. Average life is 70 hrs. Double filter masks are better, but are more expensive to buy and have added filter costs.

Respirators with canisters are readily available, inexpensive and easy to use, have proper contour fit and are approved for dust and mists. However, canister-type respirators are less comfortable to use. A hose lies between person and work place. It is hard to find replacement filters. They are typically mail order items which are expensive. Many dangerous toxins are not filtered, such as isocyanate containing finishes—all polyurethane paints and acrylics or amine containing epoxies—for boat work or fumigants or organic vapors. It is difficult to determine when paper filters lose effectiveness. A hose in front may be dangerous around machinery.

Supplied air respiration systems are the only way to protect against inhaling the vapors. However, respirators with tanks are very expensive, starting in cost at about $650. Tanks are bulky to use and are heavy. Tanks must be frequently refilled, resulting in lost work time. Exit valves may be contaminated with airborne paints and glues.

To remedy those problems, it is common for individuals or organizations to ignore the problems, to use simple ineffective masks, to use filtering equipment with cumbersome and expensive filters and absorbent canisters, or to use self-contained air respiration systems which have nearly prohibitive costs. A need exists for a system which protects against inhalation of harmful vapors or suspended particulate matter, and which can be inexpensively manufactured and sold. Many of today's system are not only expensive, but are unnecessarily heavy or bulky or otherwise hinder individual movement. A need exists for an inexpensive lightweight fresh air respiratory system which provides freedom of motion.

Another problem with current respiratory systems lies in the complicated mechanisms used. The systems have a tendency to break down and/or are very difficult to install, as well as being overly expensive. A need exists for a system which is relatively simple in design and manufacture, thus enabling ready installation and averting costly malfunction.

SUMMARY OF THE INVENTION

To overcome problems of the prior art, the present invention incorporates an intake, a mask, air tubes and a window mount. The mask slips over the head and covers the mouth and nose. The intake has a main inlet tube which splits into two side tubes, the right and left side tubes, which respectively are placed on the right and left sides of the user's head and enter the mask on opposite sides of the user's face. A lower portion of the user's head is surrounded by the mask and side inlet tubes. Preferably, adjustable head and neck straps hold the mask tightly on the user's face.

In an alternate embodiment, the mask also covers the eyes. The system can be fitted with a welder's-type mask covering substantially the whole head. The head end of the tube splits into the side inlets, which connect to the mask. The tube has a distal end with a fitting for attachment to a window mount. The distal end of the main inlet tube extends through or is connected to the mount for access to air on the outer side of a window, for example, a double hung window. The mount incorporates a securing means for securing the mount within the window opening, and a holding means for holding the distal end of the tube.

In a one embodiment, the mount incorporates a fan or venturi.

An air conditioner may dampen or dry, heat or cool outside air for moving air into the tube and subsequently toward the mask. The flow created by the positive pressure device assists the user in inhaling and, further, avoids contamination of air in the tube if the tube is punctured, due to the outflow of air at the puncture.

The tube or mount has an inlet opening at its outer end, and a screen or filter can be placed therein to filter contaminants prior to the air entering the intake. The cross-sectional area of the tube is sufficient to prevent excessive frictional losses and pressure drop. The volume of air held in the tube and lateral feeders near the user's head is sufficiently large to provide aspiration of normal quantities or air using normal non-conscious diaphragm effort by a worker having increased air uptake due to physical work. A pressure sensitive, weighted or preloaded valve may be used to exhaust exhaled air from the mask.

The tube may accommodate a speaker wire on top of the tube. A speaker near an ear or earphones may be connected to the speaker wire to communicate with the worker or to provide background sounds, instruction or music.

The window mount can be one of various embodiments. A preferred embodiment incorporates a clip on the distal end of the tube for fastening to the window sill or window pane. Another preferred embodiment provides a portable rectangular closed cell foam block having a length approximating the width of a window sill. Preferably, the foam block is securely fitted within the sill, and the window pane is raised or lowered to securely nest on the top or bottom of the block. Because of the nature of foam, the block substantially molds to the contours of the sill and window, thus providing a barrier to matter entering or leaving through the window. The block preferably has at least one hole for holding the distal end of the tube and for allowing air flow through the tube from one side of the window to the other. A series or preformed or blocked holes can be provided to allow plural inlet tubes and masks for several workers to use the same window mount.

In one form of the invention, the foam block is made universally longer than common sill lengths so that it may be trimmed by saw or knife to tightly fit within a window casing. One hole is formed through the block, and the block is partially lanced to facilitate pushing additional tubes through the block. Ends of tubes are slit so that tangs may be bent outward to prevent withdrawal of the tubes through the block.

In a preferred embodiment, the mask incorporates intake and exhaust valves to ensure proper inhalation and exhalation of fresh and spent air. Two flapper valves may be held gravitationally or by weak magnets to permit air to move from an intake to nose and mouth and from the nose and mouth through an exhaust port.

In one preferred embodiment, the system incorporates dual exhaust and inlet tubes. The inlet tube supplies fresh air to the mask, and the exhaust tube allows flow of spent air from the mask. One way check valves allow channelling of the fresh air and used air to and from the appropriate tubes. The exhaust tube can run colinearly or coaxially with the inlet tube. The inlet fresh air tube can be placed in the interior of the exhaust tube to protect the fresh air tube against puncture.

It is understood the terms tube and hose are interchangeable in describing the system of the present invention.

The mask is preferably made of a material which can be worn for extended periods, and should be constructed of a non-allergenic material. Because of the nature of many of the jobs for which the mask would be used, a washable material is preferable. Two primary materials used are non-allergenic molded rubber or impact-resistant plastic.

A fastener or tube-securing means is preferably provided for clipping the supply tube proximal to the mask at the user's back to maintain mobility. The fastener has sufficient strength for pulling the long, light, expandable, flexible tube around without added pressure on the mask, keeping the main tube and lateral facial passages out of the way of the user's arms and hands and in alignment with the user's body.

A window mount may be replaced by manifolds and usually overhead conduits when several workers are protected by masks within the same work space.

An alternate embodiment provides an overhead or work bench height channelling mechanism or track to hold the tube above the floor or work surface between the mask and the distal end, wherein a clip, roller or similar mechanism is mated with a channel or track overhead to enhance mobility and keep the main tube off the floor. A clip and clothes line apparatus also works well with the present invention.

One preferred embodiment incorporates a window mount which is adjustable for varying sizes of windows. The window mount is longitudinally adjustable, having one extension which slides within another extension with the top and bottom, maintaining proper alignment for mating with the window sill and window sash. The longitudinally expanding apparatus slides outward or inward so that the ends fit snugly against the sides of the window sill. A ratchet holds the sliding pieces in extended position until released intentionally. One embodiment incorporates mated male and female fabricated extensions. One extension has an end cap with a connection for the distal end of the main tube. A fan or jet flow venturi may be incorporated into the end cap for drawing air into the end cap from the exterior or from an air conditioning system and forcing air into the main tube. The longitudinal extensions may be fabricated plastic or metal and can be provided with weatherstripping to ensure integrity of the fit between the mount and the window sash and sill.

Another embodiment provides a blow-molded mount having two longitudinally mated extensions. Various tubes can be clipped on to one another so that tubes can be joined and decoupled.

The preferred system for providing air to contaminated areas has an air mask covering the nose and the mouth, a head strap attached to the mask for holding the mask firmly over the user's nose and mouth, and right and left inlet tubes connected to the mask and extending around right and left sides of the user's head. The right and left inlet tubes connect behind the user's head to a main inlet tube. The main inlet tube is flexible in nature and has a distal end connected to a releasable window mount.

The window mount preferably has a main inlet hose engagement means for holding the distal end of the main inlet hose and allowing passage of air through an inlet aperture at the main inlet hose distal end.

The mount can be a block for fitting within a window, with the hose engagement means being a hole provided within the block for connection to the distal end for allowing exterior communication to the inlet aperture.

Another preferred mount incorporates a clip for attaching to the window.

A preferred window mount is adjustable to fit various window sizes. The adjustable mount is a longitudinally adjustable block which fits longitudinally within the width of a window sill and expands or contracts to fit substantially the entire width of the sill. The mount maintains consistent upper and lower surfaces for mating with a movable window pane and the window sill. Weatherstripping is provided for creating a substantially impermeable seal between the window and the mount.

A fine mesh screen is provided on the distal end of the main inlet tube for filtering contaminants entering the tube when there is airborne dust or pollen outside or when flying bugs are present. A preferred system incorporates a positive air pressure provider for moving air through the main inlet tube toward the mask. The provider can be a fan within the system for drawing air exteriorly into the distal end and main inlet tube, and further into the mask. The fan can be provided within the mount. Alternatively, an air conditioner is provided within the system for providing conditioned air to the mask.

A preferred mask incorporates an eye protector. Incoming air flows along the eye portion to defog the mask.

A body-securing means is employed to attach the tube to the user's back.

Masks of the invention incorporate exhaust valves allowing users to exhaust spent air from the mask.

The mask incorporates one way intake valves for allowing fresh air into the mask and blocking exhaled air from flowing back into the inlet tubes. Straps on the mask hold the mask to the head and are adjustable to fit a variety of users.

In a preferred embodiment, the integrated breathing system apparatus has a mask for covering a lower facial area of a user. A head strap is connected to the mask for holding the mask over the nose and mouth of a user. A proximal end of an elongated air tube is connected to the mask, and a distal end of the air hose extends through a window. The tube is flexible, lightweight and form-sustaining, and has a large open lumen for freely flowing air from the distal end to the proximal end, with low pressure difference between the ends for supplying ambient air from outside a window through the tube to the mask in sufficient volume to allow normal inhalation.

The mask can have a neck strap for surrounding a back of a lower portion of the head to hold the mask firmly against a jaw of a wearer.

The proximal end of the tube is preferably bifurcated with a "Y" coupling, forming first and second supply tubes which extend from the "Y" coupling to first and second sides of the mask for balancing the mask on a head of a user, and for providing large volumes of air close to the nose and mouth of the user for effortless inhalation. A preferred mask has an exhaust valve in the mask to exhaust air exhaled by the user.

In another embodiment, the exhaust and inlet valves are in inlet and exhaust tubes. A proximal end of the inlet tube is connected to the mask, and a proximal end of the exhaust tube is connected to the exhaust valve. Distal ends of both tubes extend through a window. The inlet and exhaust tubes can be concentric, with the inlet tube inside the exhaust tube or the exhaust tube positioned inside the inlet tube. Two side by side tubes forming a figure eight cross-section are preferred.

A foam block mount can be configured for positioning between a horizontal window frame member and vertical window frame members and a horizontal edge of a window sash or sill. The block has at least one tube plug extending through the foam block. The tube plug has connector and external ends. A connector end of the tube plug receives a distal end of the tube, and the exterior end of the tube plug has a screen mounted thereon.

The integrated breathing system of the present invention is moderate in cost, between $40 and $100 depending on features and manufacturing efficiencies. The new mask and system are lightweight, with a simple and efficient design. It is inexpensive to manufacturer and is filterless. The system is built to last and is washable. It has a closed loop design. Contaminated air never comes in contact with air flow valves. Paints and glues foul conventional mask systems. The present invention protects against airborne solvents, vapors and minuscule particulates of dust. It meets all MISHA, OSHA and NIOSH standards and can be used against isocyanates, i.e. polyurethanes, amine containing epoxies (boat paints), organic vapors and fumigants. The invention provides the same protection for a longer time and at a far lower cost than respirators with tanks, and far exceeds effectiveness and operating economies of filter respirators. The new system is inexpensive and has no continuing expense, as with filter and compressed air systems.

The new integrated breathing system is comfortable, is sturdy and washable, and the straps adjust quickly. The enclosed loop prevents materials such as glues and paints from clogging valves. The system is ergonomically designed. The mask remains comfortable, while tightly fitting the contours of the face, regardless of head movement. The outflow tube surrounds the intake valve, protecting it and providing protective encasement. If an auxiliary low voltage fan is used, positive PSI provides additional protection. The system has superior air flow and is easy to use. Hoses stay out of the way of work space and hands. The air tube may be linked to other power lines (pneumatic, electrical, etc.). The system can accommodate speaker wires for factory/workshop communication.

Contaminated work spaces can be enclosed to protect other workers. There is no need for ventilation to other spaces. This system lowers vapor emissions.

The integrated breathing system solves many problems, helping the worker and improving the work environment. Contaminated areas may be effectively isolated from other work areas. The need to ventilate an entire work area is eliminated. Most work areas require "umbilical cords" for power sources, either electrical or compressed air. They do not impede work effectiveness. The integrated breathing system hose can be attached to other work "umbilical cords". If the integrated breathing system were used, for example, in a spray booth, the spraying work area could be enclosed. The business would, as a result, have a cleaner work environment and avoid ventilation legal issues with which it is now confronted.

The integrated breathing system offers several mounts: casement window, door, window (permanent) and mobile (outdoor). A preferred system has an egress screen, a stackable window mount, and a multiple window mount. The same module may be used for multiple hoses. The versatile mounting system can be mounted in door frames. Air tubes can be fitted into any door, outside opening or window. Preferably the system declips at a worker's hip.

These and further and other objects and features of the invention are apparent in the disclosure, which includes the above and ongoing written specification, with the claims and the drawings.

BRIEF DESCRIPTION OF THE DRAWINGS

FIG. 1 is a perspective of the integrated breathing system of the present invention, showing mask, side tubes, main inlet tube and window mount.

FIG. 2 shows an elevated perspective of a preferred window mount.

FIG. 3 shows an elevated view of an adjustable fabricated mount having an end cap for connection to the tube.

FIG. 4 shows an alternate blow molded mount having a tube connection means, air-receiving aperture, accordion fold adjustment means, and male and female extensions.

FIG. 5 is a side view of a preferred clip-on window mount.

FIG. 6 is a perspective of the clip-on window mount attached to a window.

FIG. 7 shows a cross-section disclosing the simplicity of design of a preferred window mount.

FIG. 8 shows a window mount and connected tube having a fan provided for creating positive pressure flow on the mask.

FIG. 9 shows a cross-section of a mount incorporating an exterior hood.

FIG. 10 is a perspective of the hood.

FIG. 11 shows a front view of the mount inserted in place of an individual pane of glass.

FIG. 12 shows a wall mount incorporating an exterior screen for filtering particulate materials prior to entering the tube.

DETAILED DESCRIPTION OF THE DRAWINGS

Figure 13:
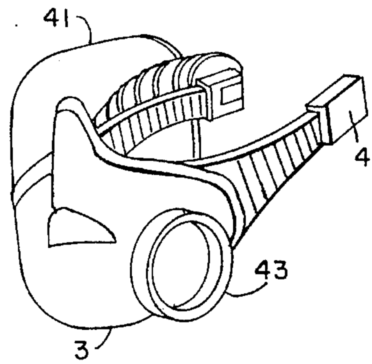
FIG. 13 shows a preferred mask having exhaust valves for exhausting spent air.

A preferred integrated breathing system of the present invention is generally indicated by the numeral 1 in FIG. 1. The system 1 incorporates a mask 3 having right and left inlet tubes 7 and 5 respectively extending from the sides of the mask 3 and joining at the back so as to surround the user's head. A main inlet tube 9 meets the side inlet tubes where they join and extends to a window mount 11 mounted within a window 13. The mask 3 preferably incorporates adjustable head strap 4 and neck strap 6 for holding the mask snugly over the user's mouth and nose.

A preferred window mount 11 shown in FIG. 2 incorporates a foam block 14 having a main tube connection means 15, with an exterior end 16 on which is attached a fine mesh screen 17. Connection tube holder openings 19 are formed or partially formed as a holding means 19 shown by the dashed circles in the mount 11 to receive connection tubes for accommodating the distal ends (not shown) of the main portable inlet tubes 9 in the foam block 14. Tubes may be pushed through the block, pushing out plugs which are reusable to close the openings when reusing the block with fewer tubes.

In a preferred embodiment in FIG. 2, the window mount 11 is constructed of a semi-elastic material such as foam, so that when inserted in a window sill with the window sash lowered or raised to meet the lower or upper surface 21 or 22, the foam will conform to the surfaces of the sill and sash to provide an air barrier between the interior and exterior of the window.

An alternative adjustable mount 11 shown in FIG. 3 allows for insertion of the mount into varying sizes of windows. Female extension 25 mates with male extension 27 to provide a longitudinally sliding connection. An end cap 23 incorporates the connection tube 15 which has an exterior end with a fine mesh screen. The end cap 23 can incorporate a fan or air conditioner attachment interiorly for drawing air through the screen and forcing it through the connection means 15 to create positive pressure into the main tube 9. The main tube 9 has a distal end 18 with an inlet aperture 20 for mating with the connection tube 15. Outward bent tangs mechanically hold the tube end 18 on the connection tube until the tube end 18 is squeezed to align the tangs with the connection tube wall for relative sliding. Alternatively, the distal end 18 can fit within the circular holder 19 in FIG. 2 for exterior extension, and further the inlet aperture 20 can be connected to a screen and/or a fan or air conditioner.

FIG. 4 shows another embodiment of the mount 11 having mated longitudinally sliding extensions 25 and 27 with interfitting accordion adjustment means 29. In this embodiment, the structure is blow molded, is hollow, and can be fitted with a fan or an air conditioner connection. The embodiments shown in FIGS. 3 and 4 may be made of fabricated material, such as plastic or metal. The adjustable structures can be fitted with weatherstripping to ensure integrity of the seal.

FIGS. 5 and 6 show an alternate window mount providing a simple design and installation. The mount 11 incorporates the connector 15, exterior end 16 and screen 17, as well as a clip 31 for attachment to a movable sash of the window. Other variations of the clip attach to the window sill, and foam strips block air flowing through the crack resulting from the window not being able to fully close. This present embodiment has the advantage of simple design and inexpensive manufacture, as well as compactness for easy storage and transportation. FIG. 7 shows a cross-sectional view of the window mount showing the simplicity of a sill mounting. The mount 34 may be a molded structure or fabricated using other conventional materials to provide a pocket or ridges for holding a connector end of a tube.

FIG. 8 shows a preferred embodiment of the present system incorporating a positive pressure device 35, which is preferably a fan, air conditioner or respirator. The fan 35 can be provided proximal the distal end of the tube 9. In one embodiment, the fan 35 connects to or is held within the mount 11. A power cord 7 easily extends to a nearby outlet. Alternatively the exteriorly placed conditioner 35, because of the low wattage needed to provide positive air pressure to the tube 9 and mask, may be solar powered.

FIGS. 9 and 10 show the mount 11 with an attached hood 39 at least partially shielding the access to the tube.

In an alternate embodiment as shown in FIG. 11, the window mount 11 can be constructed so as to replace an individual pane of glass in a window 13. This mount 11 could be clipped, clamped or otherwise fastened to the window pane and provided with a spring-mounted mechanism (not shown) to recover the receiving holes for the distal end of the tube when the system is not in use. That would allow for leaving the mount in the glassless pane with the tube not inserted for extended periods of time.

FIG. 12 shows an exterior view of the mount 11 having a clip 31. The mount 11 may alternatively incorporate a clamp or other releasable mechanism for attachment to the window sash or window sill, or may be sized to fit existing exterior exhaust tubes such as dryer vents. As shown in FIG. 12, a preferred clip-on mount 11 incorporates an exterior screen 17 to remove contaminants prior to entrance into the exterior end 16.

FIG. 13 shows an alternative mask 3 having an eye protection means 41, preferably constructed of a clear plastic, glass or similar substance. It is preferable that the eye protector 41 be constructed of a shatter-resistant, cleanable material, and various sizes and shapes of the protector providing varying degrees of protection to the upper face and eyes is not beyond the scope of the present invention. The mask 3 typically covers the nose and mouth of the user, and generally covers the user's lower face. A preferred embodiment incorporates exhaust valves 43 which exhaust spent air, and check valves (not shown) in the side inlet tubes or main inlet tube for preventing backflow of spent air. The exhaust valves are preferably one way valves, such as those used with Self-Contained Underwater Breathing Apparatus (SCUBA). A neck strap 45 can be provided in place of the head strap 4 or in conjunction with the head strap to maintain stability of the mask and ensure a firm fit. An alternative means to exhaust spent air would involve providing an exhaust tube colinearly with the inlet tubes, wherein the exhaust tube can be placed inside of the inlet tube.

Figure 14:
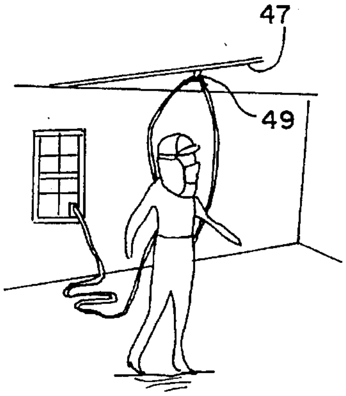
FIG. 14 discloses the system in use incorporating an overhead track for enhancing mobility.

FIG. 14 shows the system in use, wherein a track 47 and track mount 49 are provided to elevate the main inlet tube to enhance mobility for the user.

Figure 15:
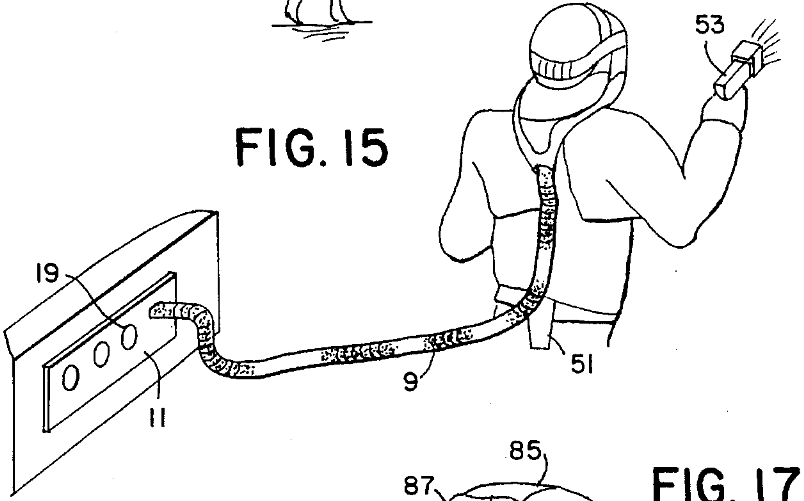
FIG. 15 shows the system in use with the wall mount incorporating plural plug-ins allowing plural users to use the same mount and window.

FIG. 15 shows the system in use, wherein the mount 11 incorporates plural hose-receiving apertures 19. A fastener 51 is attached to the main inlet tube 9, and further to a user's belt to secure the tube 9 proximal to the user to keep it out of the way for operation of implements such as a paint gun 53.

Figure 17:
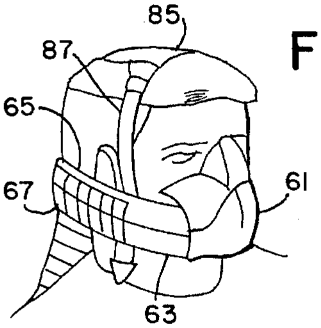
FIG. 17 is a perspective view of a preferred mask mounted on a user's head.
Figure 16:
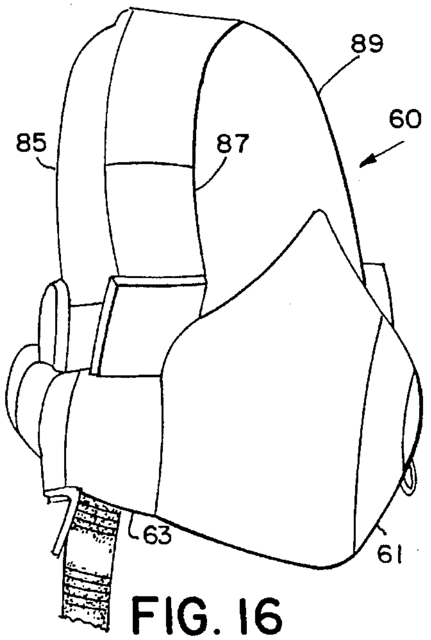
FIG. 16 is a perspective view of a preferred mask.
Figure 18:
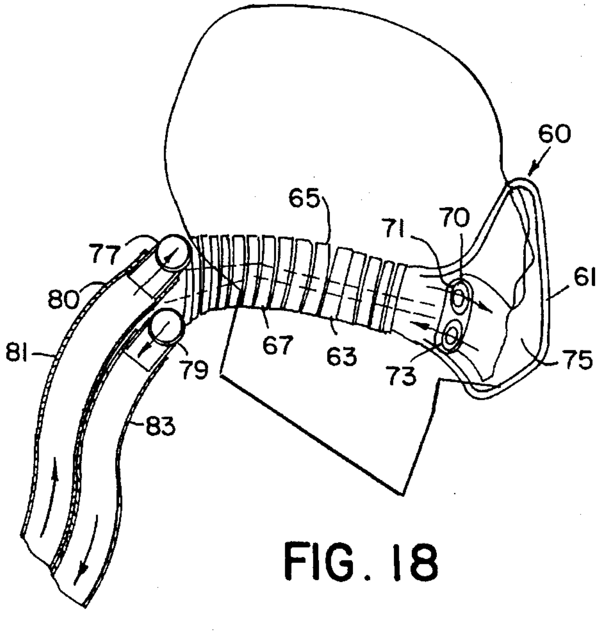
FIG. 18 is an elevation partially in section of a mask mounted on a user.

The preferred mask 60 shown in FIGS. 16, 17 and 18 has a face and nose covering portion 61 and a right side 63. The right side is divided into upper and lower hose portions 65 and 67. The left side is similar and has two hose portions which join portions 65 and 67 at the rear. A valve section 70 on each side has an inlet check valve 71 and an outlet check valve 73, which connect the facial volume 75 with the hose portions 65 and 67. The hose portions have "T" connectors 77 and 79 at the rear of the mask, which connect to proximal ends 80 of the twin inlet and outlet hoses 81 and 83. Strap 85 extends from the rear of the mask 60 over the top of a user's head. Right and left straps 87 and 89 extend downward from the forward end of central strap 85 to fix the mask on the user's head.

Figure 19:
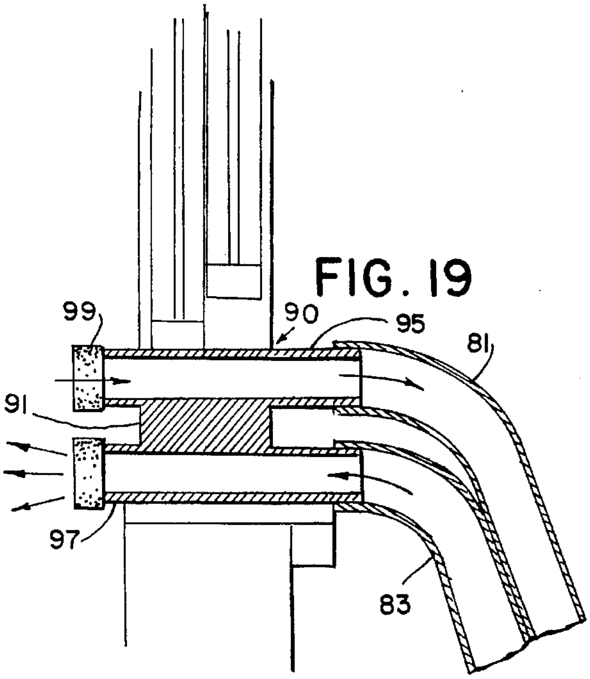
FIG. 19 is a sectional elevation of a preferred window mount.
Figure 20:
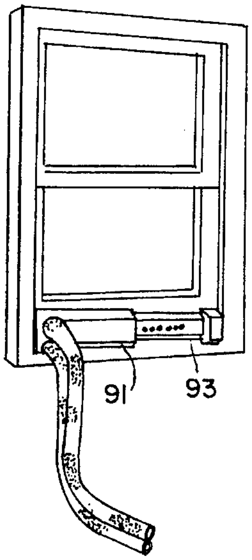
FIG. 20 is a perspective view of a preferred window mount.

A window mount 90 is shown in FIGS. 19 and 20. Fixtures 91 and 93 telescope to fill a portion of a window opening below a sash. Tubes 95 and 97 extend through fixture 91. Distal ends of tubes 81 and 83 are secured to the tubes. Screens 99 are mounted on the outer ends of the tubes. Air flow is indicated by the large arrows.

Figure 21:
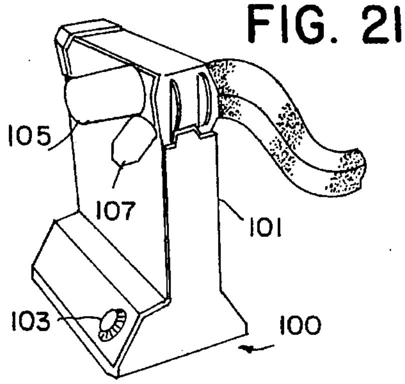
FIGS. 21 and 22 are perspective views of alternate mounting stands.
Figure 22:
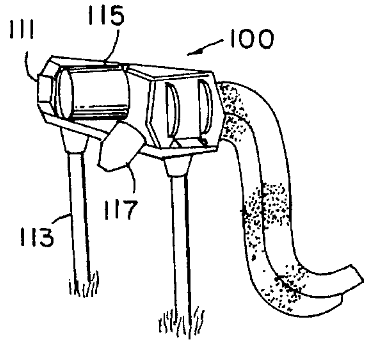

FIGS. 21 and 22 show alternate tube mounting stands 100. An air conditioner with a fan is mounted in box 101. Control 103 controls flow of air. A large screen 105 covers the inlet, and smaller screen 107 covers the outlet. Box 111 is mounted on posts 113. A fan may be included in the box. A large intake screen 115 and a smaller exhaust screen 117 extend from the box.

Figure 23:
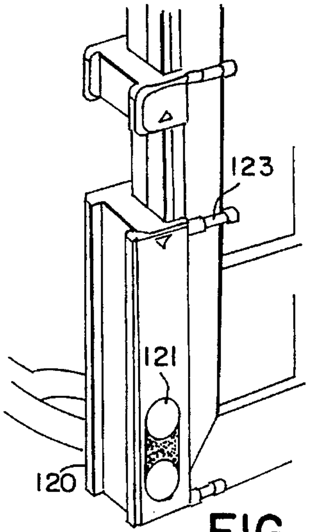
FIG. 23 is a perspective view of alternate casement mountings.
Figure 25:
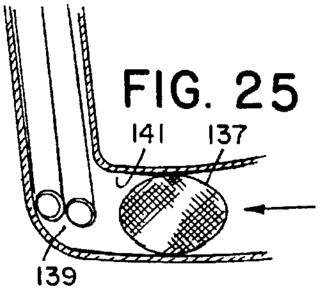
FIG. 25 is a detail of a screen which quickly covers a disconnected hose.

FIG. 23 shows a preferred casement window mounting which has a sliding telescopic holder 120 with spaces 121 for two hoses. Gripper legs 123 grip the casement window 125. The same fitting may be used on double-hung windows or on the edge of a door.

Figure 24:
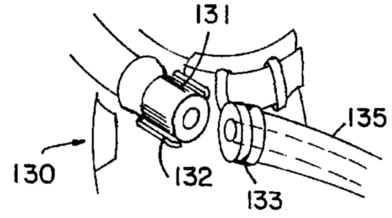
FIG. 24 is a schematic view of a hip-mounted quick disconnect coupling

FIG. 24 shows a belt-mounted quick disconnect coupling 130. Prongs 132 on the male coupling 131 engage the free end 133 of the hose 135. When the hoses are disconnected a screen 137 may slide over the ends 139 of the belt-attached hoses. A track 141 may facilitate sliding. The screen may be spring-loaded to automatically cover the hose ends upon disconnect.

Figure 26:
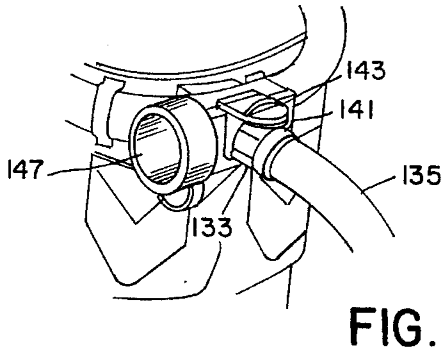
FIG. 26 shows a further detail of a hip mounted quick-disconnected tube and spring-loaded spring mount.

FIG. 26 shows additional details of the spring mount.

FIG. 26 shows the hip mount 143, the "lift" cover 145, the free end 133 of hose 135 and the screen 147. The cover 145 is lifted to connect free end 133 of hose 137. When the hose is detached the "lift" cover 145 drops, and ambient air is provided through screen 147 to the mask and via the hose, connected between the hip mount 143 and the mask.

While the invention has been described with reference to specific embodiments, modifications and variations of the invention may be constructed without departing from the scope of the invention, which is defined in the following claims.

I claim:

1. A portable system for providing air to a user in contaminated areas comprising a tight-fitting, washable, filterless air mask covering a user's nose and mouth, and having right and left sides, an adjustable head strap attached to the mask for holding the mask firmly over a user's nose and mouth, right and left air supply inlet and exhaust tubes connected to the sides of the mask and extending around right and left sides of a user's head and check valves in the mask for controlling flow from and to the inlet and exhaust tubes and the mask respectively and for preventing contact of the valves with contaminated air, and for preventing airborne materials outside the mask from clogging the valves, the right and left inlet and exhaust side tubes connecting behind a user's head to a main inlet tube and a coaxial exhaust tube, the main inlet and exhaust tubes being flexible and having distal ends connected to a releasable window mount.

2. The apparatus of claim 1, further comprising the window mount having a main inlet tube engagement means for holding the distal end of the main inlet tube and allowing passage of air through an inlet aperture at the main inlet tube distal end.

3. The apparatus of claim 2, further comprising the mount being a block for fitting within a window, the tube engagement means being a hole provided within the block for connection to the distal end for allowing exterior communication to the inlet aperture.

4. The apparatus of claim 3, further comprising the mount incorporating a clip for attaching to the window.

5. The apparatus of claim 3, further comprising the block being constructed of foam.

6. The apparatus of claim 2, further comprising the window mount being adjustable to fit various window sizes.

7. The apparatus of claim 6, further comprising the adjustable mounting means being a longitudinally adjustable block which fits longitudinally within the width of a window sill, expanding to fit substantially the entire width of the sill, yet maintaining consistent upper and lower surfaces for mating with a movable window sash and the window sill.

8. The apparatus of claim 1, further comprising a screen provided proximal the distal end of the main inlet tube for filtering contaminants entering the tube.

9. The apparatus of claim 1, further comprising the filtering system incorporating a positive air pressure provider for forcing air through the main inlet tube and into the mask.

10. The apparatus of claim 9, further comprising a fan provided within the system for drawing air exteriorly into the distal end and main inlet tube, and further into the mask.

11. The apparatus of claim 10, further comprising the fan provided with the mount.

12. The apparatus of claim 9, further comprising an air conditioner provided within the system for providing temperature conditioned air to the mask.

13. The apparatus of claim 1, further comprising the mask incorporating an eye protector.

14. The apparatus of claim 1, further comprising a body-securing means for attaching the main inlet and exhaust tubes to the user's back.

15. The apparatus of claim 14, wherein the body securing means further comprises a belt with a belt-mounted quick disconnected coupling for engaging a free end of the main inlet and exhaust tubes.

16. The apparatus of claim 14, further comprising a screen attached to the belt-mounted coupling and means for connecting the inlet and tube.

17. The apparatus of claim 1, further comprising an overhead suspension means for holding the main inlet tube suspended above a work space out of the way of the user.

18. The apparatus of claim 17, further comprising a track mechanism provided in the ceiling with the overhead suspension means connected to the track.

19. The apparatus of claim 1, further comprising the mask being made of non-allergenic molded rubber.

20. The apparatus of claim 1, further comprising the mask being made of impact-resistant plastic.

21. The apparatus of claim 1, further comprising the strap being adjustable to fit a variety of users.

22. The apparatus of claim 1, further comprising the mount incorporating a series of engagement means for fitting plural masks and connected inlet tubes to allow plural users to utilize the same work space.

23. An integrated portable breathing system apparatus comprising a tight-fitting, washable, filterless mask for covering a lower facial area of a user, an adjustable head strap connected to the mask for holding the mask tightly over a nose and mouth of the user, a closed loop air supply and exhaust connected to the mask, further comprising elongated inlet and exhaust air tubes having proximal and distal ends, proximal ends of the air tubes connected to the mask and distal ends of the air tube extending to a removable window mount, inlet and exhaust check valves within the mask and connected between the proximal ends and the mask for flowing air from the inlet tube to the mask and for flowing air from the mask to the exhaust tube respectively, and for preventing contact of the valves with contaminated air, and for preventing airborne materials such as glues and paints from clogging the valves, the tubes being flexible, lightweight and form-sustaining, and having large open lumens for freely flowing air from the distal end to the proximal end of the inlet tube and from the proximal end to the distal end of the outlet tube, with low pressure difference between the ends for supplying air from outside a window through the tube to the mask in sufficient volume to allow normal inhalation for protection against airborne solvents, vapors, minuscule particles of dust, isocyanates, polyurethanes, amine containing epoxies, boat paints, organic vapors and fumigants, wherein the inlet and exhaust tubes are concentric, wherein the exhaust tube is positioned outside the inlet tube.

24. The apparatus of claim 23, wherein the mask additionally has a neck strap for surrounding a back of a lower portion of the head to hold the mask firmly against a jaw of a wearer.

25. The apparatus of claim 23, wherein the proximal ends of the tubes are bifurcated with a coupling, forming first and second mask supply and exhaust tubes which extend from the "Y" coupling to first and second sides of the mask for balancing the mask on a head of a user, and for providing large volumes of air close to the nose and mouth of the user for normal inhalation and exhalation.

26. The apparatus of claim 23, further comprising a foam block configured for positioning between a horizontal window frame member and vertical window frame members and a horizontal edge of a window sash, and having at least one tube plug extending through the foam block, the tube plug having connector and exterior ends, an connector end of the tube plug receiving a distal end of the tube, and the exterior end of the tube plug having a screen mounted thereon.

27. A portable breathing system comprising means for preventing inhalation of airborne solvents, vapors, minuscule particles of dust, isocyanates, polyurethanes, amine containing epoxies, boat paints, organic vapors, fumigants, and the like, in contaminated areas;

the breathing system further comprising a tight-fitting, washable, filterless mask adapted to cover the nose and mouth of a wearer, an adjustable head strap attached to the mask adapted to firmly hold the mask over the nose and mouth of a wearer;

a closed loop air supply and exhaust connected to the mask comprising at least one inhalation check valve and at least one exhalation check valve, and means for preventing contact of said valves with contaminated air and for preventing particles such as glues and paints from clogging said valves, said means for preventing contact and clogging of said valves comprising right and left inlet and exhaust side tubes connected to the mask and adapted to extend along the right and left sides of the wearer's face and adapted to connect behind the wearer's head, a main inlet connected to both the right and left inlet and exhaust side tubes, the main inlet tube being covered by a coaxial exhaust tube, the main inlet tube and the coaxial exhaust tube being flexible and having distal ends; and a releasable window mount having the distal ends connected thereto, the window mount having a non-contaminated source of air on an exterior side and the contaminated area on an interior side, whereby a closed loop is defined from the exterior side of said window mount to the wearer via the main inlet tube, the right and left inlet tubes, the at least one inhalation check valve and the mask, and back to the exterior side of the window mount via the mask, the at least one exhalation check valve, the right and left exhaust tubes, and the coaxial exhaust tube.

* * * * *